United States Patent [19]

Bonner, Jr. et al.

[11] Patent Number: 4,534,354
[45] Date of Patent: Aug. 13, 1985

[54] BANDAGE

[75] Inventors: Francis J. Bonner, Jr.; Francis J. Bonner, III, both of Radnor, Pa.

[73] Assignee: Universal Medical Products, Inc., Radnor, Pa.

[21] Appl. No.: 426,406

[22] Filed: Sep. 29, 1982

[51] Int. Cl.³ .............................................. A61F 7/00
[52] U.S. Cl. ................................ 128/402; 128/156; 62/530
[58] Field of Search ............... 128/156, 158, 157, 160, 128/402, 403, 399, 169, DIG. 15; 604/291, 308, 290; 62/530

[56] References Cited

U.S. PATENT DOCUMENTS

| 1,491,539 | 4/1924 | Kirschmann | 128/402 |
| 2,577,945 | 12/1951 | Atherton | 128/156 |
| 3,161,031 | 12/1964 | Flannery | 62/530 |
| 3,736,769 | 6/1973 | Petersen | 128/402 |
| 3,871,376 | 3/1975 | Kozak | 128/403 |
| 3,880,161 | 4/1975 | Fossel | 128/169 |
| 3,889,684 | 6/1975 | Lebold | 128/403 |
| 3,929,131 | 12/1975 | Hardwick | 604/291 |
| 4,036,220 | 7/1977 | Bellasalma | 128/82 |
| 4,081,150 | 3/1978 | Tyson | 128/403 |
| 4,092,982 | 6/1978 | Salem | 128/402 |
| 4,183,226 | 1/1986 | Moore | 62/530 |
| 4,205,674 | 6/1980 | Porat et al. | 128/169 |
| 4,243,028 | 1/1981 | Puyana | 128/165 |
| 4,259,957 | 4/1981 | Sonenstein et al. | 128/DIG. 15 |
| 4,344,303 | 8/1982 | Kelly, Jr. | 62/530 |
| 4,377,160 | 3/1983 | Romaine | 128/156 |

FOREIGN PATENT DOCUMENTS 1383536 2/1975 United Kingdom .............. 128/403

OTHER PUBLICATIONS

Dr. Kirt Josefek, *Omnipak*, Healthcore Publication.
Dale Omnipak, Hot/Cold Support.

*Primary Examiner*—Henry J. Recla
*Assistant Examiner*—Karin M. Reichle
*Attorney, Agent, or Firm*—Seidel, Gonda, Goldhammer

[57] ABSTRACT

A bandage is defined by a layer of closed cell foam polymeric material sandwiched between and bonded to adjacent layers of fabric. The foam layer is thicker than the fabric layers. One of the layers of fabric is absorbent with respect to aqueous liquids and is adapted to be in contact with an area of the body.

28 Claims, 8 Drawing Figures

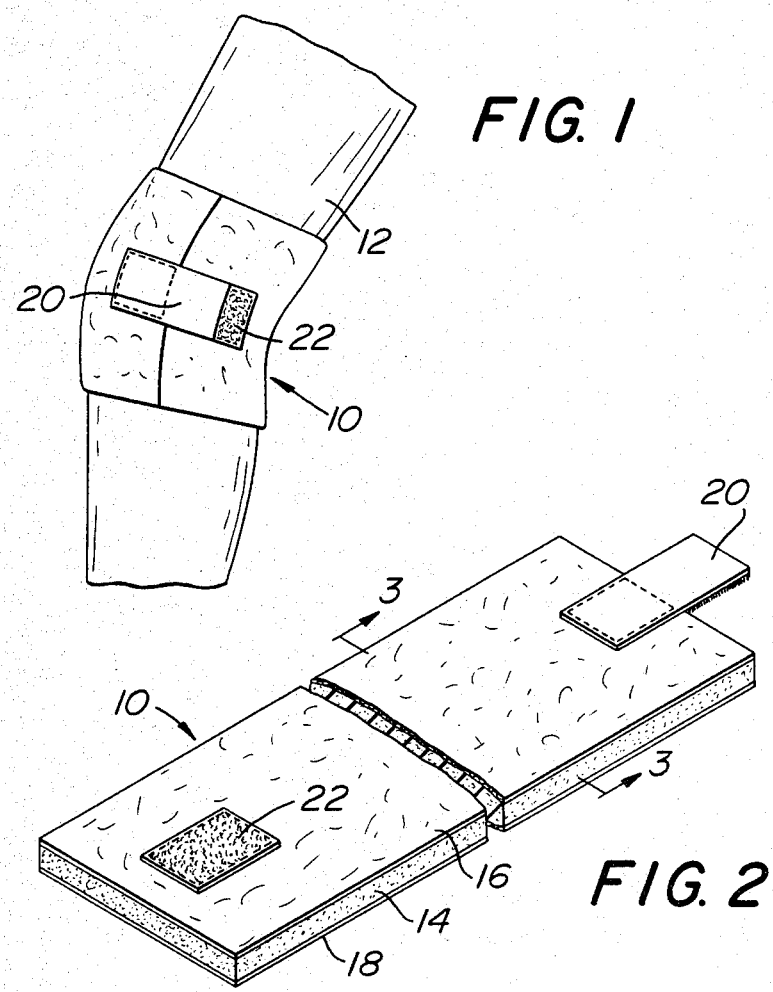
FIG. 1
FIG. 2
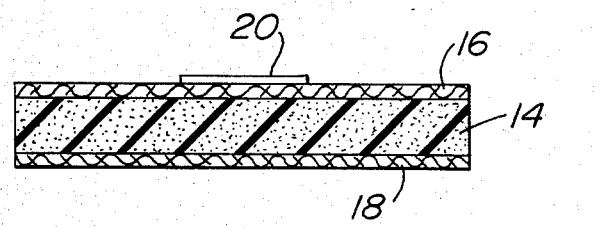
FIG. 3

BANDAGE

BACKGROUND OF THE INVENTION

The therapeutic effects of locally applied cold (cryotherapy) have been utilized by man for long periods of time. However, the mechanism of action has been poorly understood. Likewise, the use of compressive bandages has been known to control swelling and bleeding. All products currently available either rely on another device to apply compression with cold or fail to reach temperatures compatible with maximum therapeutic effects of cold, namely 0°–8° C. with 6° C. being the preferred temperature. An example of the former would include an icepack applied with an elastic bandage. An example of the latter includes gel bandages which rely on the latent heat of evaporation for skin cooling.

The present invention is directed to solution of the problem of a means for applying cold to an area of the body within a therapeutic range by way of an insulated, hygroscopic and protective material applied as a bandage.

SUMMARY OF THE INVENTION

The present invention is directed to a laminated bandage in the form of a layer of closed cell foam polymeric material sandwiched between and bonded to layers of fabric, said foam layer being substantially thicker than the layers of fabric. One of the layers of fabric is adapted to absorb water. A strap or panel may be attached to the bandage and adapted to be releasably engaged with mating structure on the other end of the bandage or on another piece of material used to secure the bandage in position against the body.

Various objects and advantages of the present invention are set forth hereinafter.

For the purpose of illustrating the invention, there is shown in the drawings a form which is presently preferred; it being understood, however, that this invention is not limited to the precise arrangements and instrumentalities shown.

FIG. 1 is an elevation view of a knee with one embodiment of the bandage of the present invention attached thereto.

FIG. 2 is a perspective view of the bandage in FIG. 1.

FIG. 3 is a sectional view taken along the line 3—3 in FIG. 2 but on an enlarged scale.

DETAILED DESCRIPTION

Figure 4:
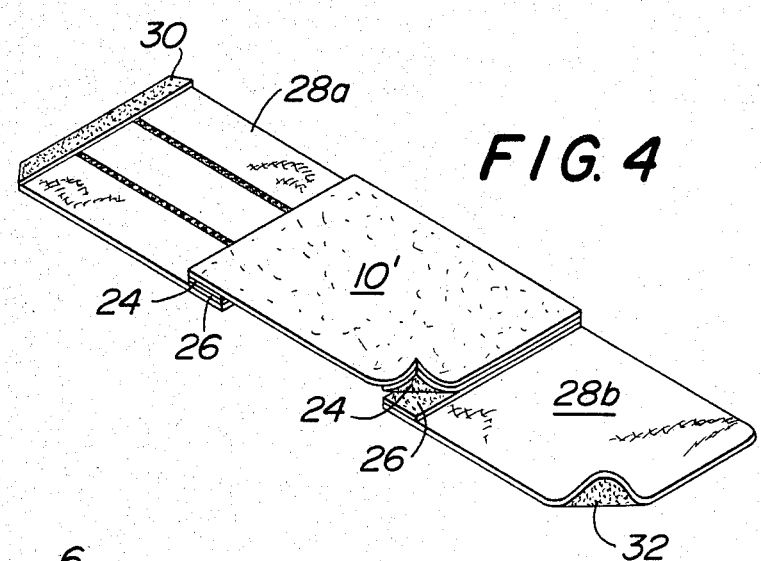
FIG. 4 is a perspective view of another embodiment of the bandage of the present invention for application to the user's back.

Referring to the drawings in detail, wherein like numerals indicate like elements, there is shown in FIGS. 1–3 a bandage in accordance with the present invention designated generally as 10. In FIG. 1, the bandage 10 is shown applied to a joint of a limb 12 such as a leg.

The bandage 10 is laminated and preferably comprises a layer of closed cell foam polymeric material 14 sandwiched between and bonded to layers of fabric 16 and 18. Layer 14 is substantially thicker than the layer 16 and 18. It is important that layer 14 be a closed cell layer. The closed cell foam may act as an insulator. The insulation properties of closed cell foams are inherently similar to other bulk insulation materials having a large number of voids. A solid material transfers heat by conduction. Whereas, an insulation material having a number of voids does not transfer heat solely by conduction, but transfers heat by a combination of conduction (through the cell walls) and convection (through the voids). The rate of convection through the void will depend on the gas within the void and the ability of the gas to move within the void. In closed cell foams, the gas cannot flow through the cell; whereas in the open cell foams, the gas may flow through the voids. The gas flowing through the voids will increase the convection rate of heat transfer. Therefore, closed cell foams are better insulators than open cell foams. Also, closed cell foams inherently do not absorb liquids as open cell foams do. Liquids may easily permeate the open cell foams. Thus, the closed cell foam will not absorb the liquid as open cell foam would, and upon subsequent cooling of the bandage, it will not become rigid. Layer 18, which is the layer adapted to be in contact with the skin, is an absorbent layer of towelling fabric such as terry cloth having longitudinal stretch. Layer 16 is preferably a woven layer of nylon or LYCRA (trademark) which is woven from spandex fibers having stretch in the longitudinal direction. Layer 16 preferably reflects cold that tends to escape through the closed cell layer back toward the terry cloth layer and slows the tendency of the bandage to warm to room temperature. The outer surface of layer 16 reflects heat and similarly slows the warming of the bandage.

By way of example and not by way of limitation, preferred thicknesses for the layers are as follows: layer 16 preferably has a thickness of 1/32", layer 14 preferably has a thickness of 3/16", and layer 18 preferably has a thickness of 1/16". Layers 16 and 18 are preferably bonded to layer 14 by application of heat and pressure. While layer 16 preferably has stretch in the longitudinal direction, it may optionally have stretch in both the longitudinal and transverse directions.

The bandage 10 has a strap 20 fixedly secured to one end in any convenient manner. Strap 20 is adapted to be releasably engaged with mating structure on the other end of the bandage such as element 22. In the preferred embodiment, the mating structure on strap 20 and element 22 are interengaging fibers of the type sold commercially under the trademark VELCRO.

The preferred manner of using the bandage of the present invention for dealing with pain resulting from a condition such as chronic arthritis or an injury is as follows. Bandage 10 is soaked in water. Only layer 16 absorbs the water. The bandage is then placed in a refrigerator and cooled to a temperature in the range of 0°–8° C. with the optimum temperature being approximately 6° C. Thereafter, the bandage is applied to the knee joint shown in FIG. 1 with sufficient tightness so as to apply pressure to the joint. Even though frozen, the bandage 10 will conform to the area being treated, and will direct cold directly to that area.

The pressure stimulates the release of endorphins by the body which provides a therapeutic effect. Endorphins are released by the cold stimulus and by the application of pressure. The foam layer 14 is an insulator which minimizes heat transfer between inner and outer surfaces of the bandage 10. The layer 16 is preferably a light or reflective color so as to reflect heat away from the bandage. The bandage 10 is sufficiently pliable to anatomically conform to the joint and will conform better as it warms up. The bandage 10 will gradually warm up to room temperature after about ½ hour.

Figure 5:
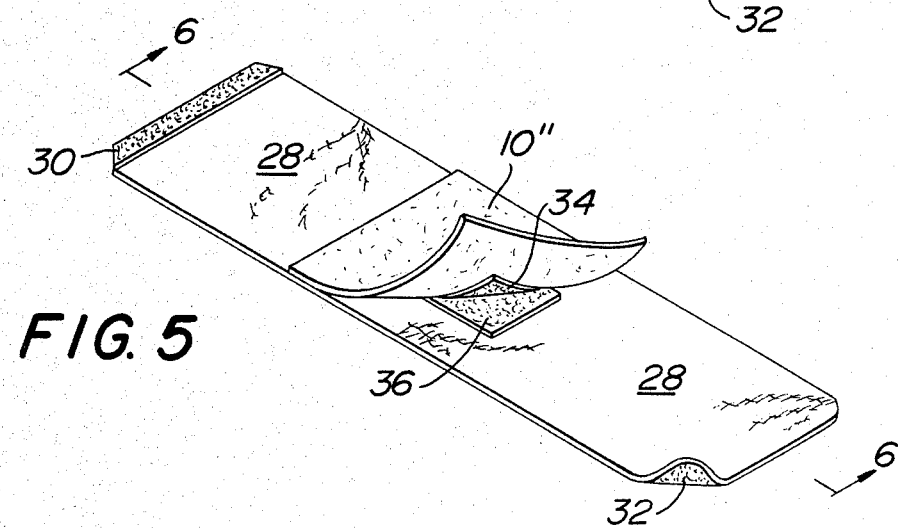
FIG. 5 is a perspective view of a further embodiment of the bandage of the present invention also for application to the user's back.
Figure 6:
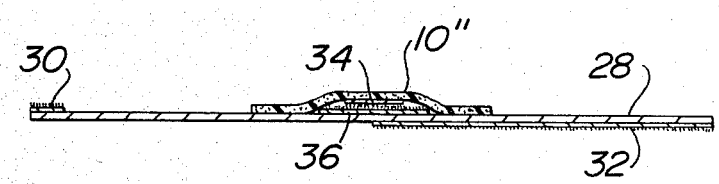
FIG. 6 is a sectional view taken along the line 6—6 in FIG. 5 but on an enlarged scale.

If desired the bandage 10 could be applied on the back of a user as shown in FIGS. 4-6. As shown in FIG. 4, the bandage 10' is provided at opposite ends with a transverse panel 24 of VELCRO material. Panel 24 may be stitched or otherwise fastened to the bottom surface of bandage 10'. Each panel 24 is adapted to be releasably engaged with an associated mating transverse panel 26 of VELCRO material stitched or otherwise fastened to the end of a strap 28a and the end of a strap 28b at one end thereof.

A transverse panel 30 of VELCRO material is also stitched or otherwise secured to the other end of strap 28a. Transverse panel 30 is adapted to be releasably engaged with the bottom surface 32 of strap 28b. Substantially the entire bottom surface 32 may be made of a material adapted to mate with and releasably engage the transverse VELCRO panel 30 so as to facilitate adjustment. Thus, panel 30 may be releasably secured at a variety of locations along bottom surface 32 according to the waist size of the user. Preferably, the strap 28a is made of an elastic material which can be stretched to enable placement of the panel 30 at selected locations along the bottom surface 32 of strap 28b.

Bandage 10' has the laminate structure shown in FIG. 3, strap 20 not included. In use, only bandage 10' need be cooled. since it is the only portion which applies cold to the back. Thus, bandage 10' may be disengaged from straps 28a, 28b and then soaked and refrigerated as previously described. Thereafter, the bandage 10' is secured to the strap end panels 24, and the straps 28a and 28b are fastened about the user's waist so that the bandage 10' contacts the injured area of the back with the desired pressure.

The bandage 10 can also be modified to be applied on the back of the user as shown in FIGS. 5-6. The bandage 10" has the laminate structure shown in FIG. 3, strap 20 not included. A panel 34 of VELCRO material is secured by stitching or otherwise to the underside of bandage 10'. Mating structure in the form of a VELCRO panel 36 is secured by stitching or the like to the upper surface of strap 28. Strap 28 is made of an elastic material such as woven nylon or LYCRA. A panel 30 of VELCRO material is secured to one end of the strap. A layer 32 made of a material adapted to mate with and releasably engage the VELCRO panel 30 is secured to the bottom surface of strap 28.

In use, the bandage 10" is removed from strap 28 and then soaked and refrigerated as previously described. Thereafter, the bandage is removed from the refrigerator and secured to strap 28 by placing the bandage over the straps such that panels 34 and 36 engage. The user places the bandage 10" on the injured area of the back and wraps strap 28 about the waist while securing panel 30 to the mating layer 32 at a location conforming to the user's waist size.

Figure 7:
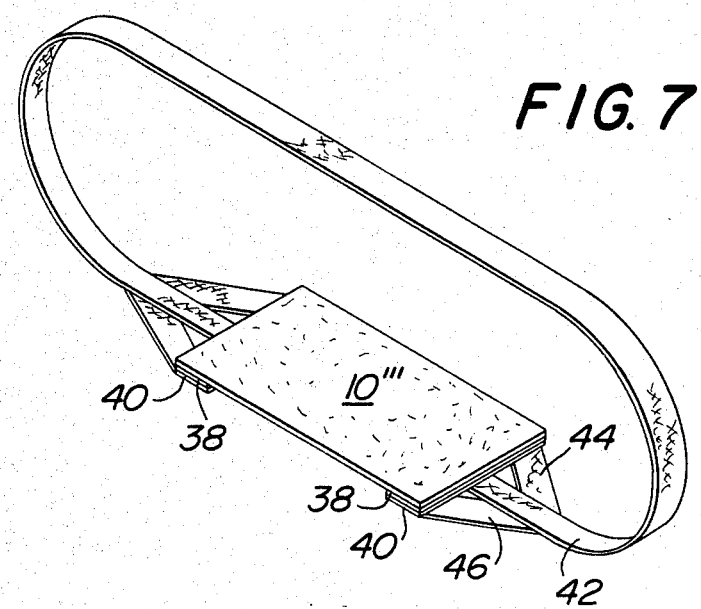
FIG. 7 is a perspective view of a further embodiment of the bandage of the present invention for application to the user's shoulder.
Figure 8:
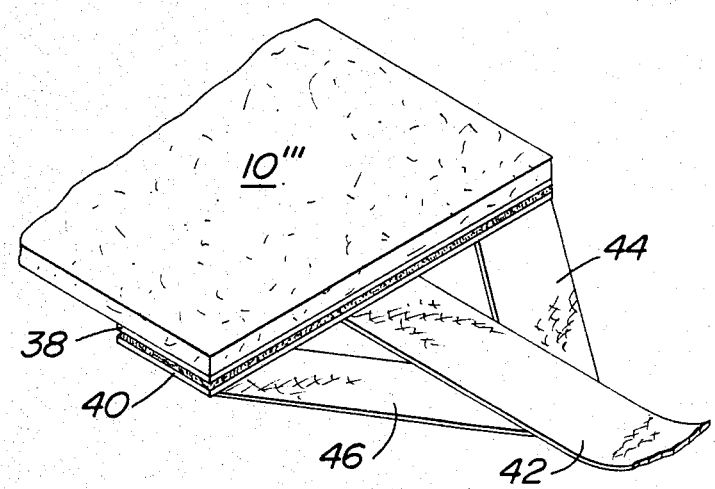
FIG. 8 is an enlarged view of the end portion of the bandage shown in FIG. 7.

A further modification of the invention is shown in FIGS. 7-8 wherein a bandage 10''' is used to treat a shoulder injury. The bandage 10''' is identical in structure to bandage 10 shown in FIG. 3, strap 20 not included.

Each end of bandage 10''' is provided with a transverse panel 38 secured by stitching or the like to the bottom surface of the bandage. Panel 38 is made of VELCRO material. Each panel 38 is adapted to be releasably engaged with mating structure in the form of a panel 40 secured by stitching or other suitable means to a body strap 42 preferably made of a non-elastic fabric material. Preferably, strap 42 is stitched or otherwise secured to strap segments 44 and 46 at each end of the bandage. The strap segments 44 and 46 are secured by stitching or other suitable means to opposite ends of the underside of each panel 40.

In use, the bandage 10''' is removed from the panels 40 and then soaked and refrigerated as previously described. Thereafter, the bandage 10''' is secured to one of the panels 40. The bandage 10''' is then applied to the injured area of the shoulder requiring treatment, and the strap 42 is wrapped about the user's chest and back and under the arm so that the bandage can be secured to the free panel 40 at the injured area of the shoulder.

The bandage can be modified for application to other parts of the body within the spirit and scope of the invention. Thus, smaller bandages could be made for application to the ankle or wrist of a user. It is apparent that many modifications could be effected so that the bandage could be applied where needed.

The present invention may be embodied in other specific forms without departing from the spirit or essential attributes thereof and, accordingly, reference should be made to the appended claims, rather than to the foregoing specification, as indicating the scope of the invention.

We claim:

1. A method of treating pain and/or inflamation at an area of a body to cause release of endorphins comprising:
   a. providing a laminated bandage having a layer of closed cell foam polymeric material, two layers of fabric of substantially the same size as said layer of closed cell foam, said layer of closed cell foam sandwiched between and bonded to said layers of fabric, one of said layers of fabric being absorbent with respect to aqueous liquids and adapted to be in contact with an area of the body, said foam layer being substantially thicker than the fabric layers and having a substantially constant thickness along a substantial length thereof,
   b. contacting said bandage with a liquid, then cooling said bandage to a temperature close to but slightly above the freezing temperature of said liquid,
   c. applying the cooled bandage to the area of the body with said layer of fabric in contact with the skin thereof and in an overlapping manner, and securing the bandage in position at said area with a compressive force on the area of the body so that the area is subjected to both pressure and cold to cause release of endorphins.

2. A method in accordance with claim 1 including all layers being stretchable in a lengthwise direction with respect to the bandage.

3. A method in accordance with claim 1 wherein the bandage is contacted with water and then cooled to a temperature of about 0° C.-8° C. before being applied to the body.

4. A bandage for reducing pain comprising:

an elongated layer of closed cell foam polymeric material;

two layers of fabric of substantially the same size as said layer of closed cell foam, said layer of foam sandwiched between and bonded to said layers of fabric, one of said layers of fabric being absorbent with respect to aqueous liquids and adapted to be in contact with a body portion, said foam layer being substantially thicker than the fabric layers and having a substantially constant thickness along a substantial length thereof;

means for fastening at one end of the bandage;

and mating means at the opposite end of the bandage for releasably engaging said fastening means to thereby secure the bandage to the body portion and apply pressure thereto, and all layers adapted to be stretchable in a lengthwise direction with respect to the bandage whereby said liquid absorbent layer is to be first soaked with liquid, the bandage then cooled to a temperature close to but slightly above the freezing temperature of the liquid, and the bandage then applied to the body portion with the absorbent layer in contact therewith and secured thereto such that the bandage applies pressure to the body portion.

5. A bandage in accordance with claim 1 wherein said one absorbent layer of fabric is the only layer which is absorbent.

6. A bandage in accordance with claim 1 wherein the other layer of fabric has a light color for reflecting heat and cold.

7. A bandage in accordance with claim 1 wherein the one absorbent layer of fabric is terry cloth, and the other layer of fabric having a light reflective color.

8. A bandage in accordance with claim 1 wherein said means includes a strip of elastic material attached to the opposite end of said bandage and forming an extension thereof, said elastic strip having engagement means thereon for matins the fastening means on said bandage and a width substantially equal to the width of said bandage.

9. A bandage for reducing pain comprising:
a layer of closed cell foam polymeric material;
two layers of fabric of substantially the same size as said layer of closed cell foam, said layer of closed cell foam sandwiched between and bonded to said layers of fabric, one of said layers of fabric being absorbent with respect to aqueous liquids and adapted to be in contact with an area of the body, said foam layer being substantially thicker than the fabric layers and having a substantially constant thickness along a substantial length thereof;
a first piece of material adapted for releasable securement to one end of said bandage;
a second piece of material adapted for releasable securement to the opposite end of said bandage;
mating structure located at both ends of said first piece of material;
mating structure located at both ends of said second piece of material; and
a discrete mating means at each end of the bandage for releasably engaging with the mating structure on one end of said first piece of material and the mating structure on one end of said second piece of material, and the mating structure on the other end of said first piece of material and the mating structure on the other end of said second piece of material adapted for releasable engagement with each other whereby said liquid absorbent layer is to be first soaked with liquid, the bandage then cooled to a temperature close to but slightly above the freezing temperature of the liquid; and the bandage then applied to the area of the body with the absorbent layer in contact therewith and secured thereto such that the bandage applies pressure to the area of the body.

10. A bandage in accordance with claim 9 wherein all layers have stretch in a lengthwise direction with respect to the bandage.

11. A bandage in accordance with claim 10 wherein said one absorbent layer of fabric is the only layer which is absorbent.

12. A bandage in accordance with claim 9 wherein the other layer of fabric has a light color for reflecting heat and cold.

13. A bandage in accordance with claim 9 wherein said one absorbent layer of fabric is terrycloth, and the other layer of fabric adapted to be stretchable in a lengthwise direction with respect to the bandage and having a light reflective color.

14. A bandage for reducing pain comprising:
a layer of closed cell foam polymeric material;
two layers of fabric of substantially the same size as said layer of closed cell foam, said layer of closed cell foam sandwiched between and bonded to said layers of fabric, one of said layers of fabric being absorbent with respect to aqueous liquids and adapted to be in contact with an area of the body, said foam layer being substantially thicker than the fabric layers and having a substantially constant thickness along a substantial length thereof;
a piece of material longer than said bandage and sufficiently long so that said longer piece is adapted to encircle the area of the body and apply pressure thereto;
mating means located at ends of said longer piece; and
mating means secured to the bandage and adapted to releasably engage with said mating means on said longer piece of material whereby said liquid absorbent layer is to be first soaked with liquid, the bandage then cooled to a temperature close to but slightly above the freezing temperature of the liquid, and the bandage then applied to the area of the body with the absorbent layer in contact therewith and secured thereto such that the bandage applies pressure to the area of the body.

15. A bandage in accordance with claim 14 wherein all layers have stretch in a lengthwise direction with respect to the bandage.

16. A bandage in accordance with claim 15 wherein said one absorbent layer of fabric is the only layer which is absorbent.

17. A bandage in accordance with claim 14 wherein the other layer of fabric has a light color for reflecting heat and cold.

18. A bandage in accordance with claim 14 wherein said one absorbent layer of fabric is terrycloth, and the other layer of fabric adapted to be stretchable in a lengthwise direction with respect to the bandage and having a light reflective color.

19. A bandage for reducing pain comprising:
a layer of closed cell foam polymeric material;
two layers of faebric of substantially the same size as said layer of closed cell foam, said layer of closed cell foam sandwiched between and bonded to said layers of fabric, one of said layers of fabric being absorbent with respect to aqueous liquids and adapted to be in contact with an area of the body, said foam layer being substantially thicker than the fabric layers and having a substantially constant thickness along a substantial length thereof; and means on the bandage for securing the bandage in position and applying pressure to the area of the body whereby said liquid absorbent layer is to be first soaked with liquid, the bandage then cooled to a temperature close to but slightly above the freezing temperature of the liquid, and the bandage then applied to the area of the body with the absorbent layer in contact therewith and secured thereto such that the bandage applies pressure to the area of the body.

20. A bandage in accordance claim 25 wherein all layers have stretch in a lengthwise direction with respect to the bandage.

21. A bandage in accordance with claim 20 wherein said one absorbent layer of fabric is the only layer which is absorbent.

22. A bandage in accordance with claim 19 wherein the other layer of fabric has a light color for reflecting heat and cold.

23. A bandage in accordance with claim 19 wherein said one absorbent layer of fabric is terry cloth, and the other layer of fabric adapted to be elastic at least in part so as to be stretchable in a lengthwise direction with respect to the bandage and having a light reflective color.

24. A bandage for reducing pain comprising:
a layer of closed cell foam polymeric material; two layers of fabric of substantially the same size as said layer of closed cell foam, said layer of closed cell foam sandwiched between and bonded to said layers of fabric, one of said layers of fabric being absorbent with respect to aqueous liquids and adapted to be in contact with an area of the body, said foam layer being substantially thicker than the fabric layers and having a substantially constant thickness along a substantial length thereof;

means for securing the bandage in position at and applying pressure to the area of the body; and means for removably securing said bandage to said securing means whereby said liquid absorbent layer is to be first soaked with liquid, the bandage then cooled to a temperature close to but slightly above the freezing temperature of the liquid, and the bandage then applied to the area of the body with the absorbent layer in contact therewith and secured thereto such that the bandage applies pressure to the area of the body.

25. A bandage in accordance with claim 24 wherein all layers have stretch in a lengthwise direction with respect to the bandage.

26. A bandage in accordance with claim 25 wherein said one absorbent layer of fabric is the only layer which is absorbent.

27. A bandage in accordance with claim 24 wherein the other layer of fabric has a light color for reflecting heat and cold.

28. A bandage in accordance with claim 24 wherein said one absorbent layer of fabric is terry cloth, and the other layer of fabric adapted to be stretchable in a lengthwise direction with respect to the bandage and having a light reflective color.

* * * * *